US005447958A

United States Patent [19]

[11] Patent Number: 5,447,958

[45] Date of Patent: Sep. 5, 1995

Niigata et al.

[54] SULFAMOYL-SUBSTITUTED PHENETHYLAMINE DERIVATIVES, THEIR PREPARATION, AND PHARMACEUTICAL COMPOSITIONS, CONTAINING THEM

[75] Inventors: Kunihiro Niigata; Takashi Fujikura, both of Saitama, Japan

[73] Assignee: Yamanouchi Pharmaceutical Co., Ltd., Tokyo, Japan

[21] Appl. No.: 314,322

[22] Filed: Sep. 28, 1994

Related U.S. Application Data

[60] Division of Ser. No. 174,608, Dec. 28, 1993, Pat. No. 5,391,825, which is a division of Ser. No. 68,595, May 28, 1993, abandoned, which is a continuation of Ser. No. 847,842, Mar. 9, 1992, abandoned, which is a continuation of Ser. No. 658,109, Feb. 20, 1991, abandoned, which is a division of Ser. No. 425,708, Oct. 23, 1989, abandoned, which is a continuation-in-part of Ser. No. 294,924, Jan. 5, 1989, abandoned, which is a continuation of Ser. No. 105,459, Oct. 2, 1987, abandoned, which is a continuation of Ser. No. 828,063, Feb. 10, 1986, abandoned, which is a division of Ser. No. 803,204, Nov. 27, 1985, Pat. No. 4,731,478, which is a continuation-in-part of Ser. No. 756,790, Jul. 18, 1985, Pat. No. 4,703,063, which is a continuation of Ser. No. 632,258, Jul. 18, 1984, Pat. No. 4,558,156, which is a continuation of Ser. No. 403,006, Jul. 29, 1982, abandoned, which is a division of Ser. No. 231,421, Feb. 4, 1981, Pat. No. 4,373,106.

[30] Foreign Application Priority Data

Feb. 8, 1980 [JP] Japan .................................. 55-14382

[51] Int. Cl.$^6$ ...................... A01N 41/06; C07C 311/10

[52] U.S. Cl. ........................................ 514/603; 564/86

[58] Field of Search ............................ 564/86; 514/603

*Primary Examiner*—José G. Dees

*Assistant Examiner*—Joseph Conrad

*Attorney, Agent, or Firm*—Ryan and Wayne Burgess

[57] ABSTRACT

Pharmaceutical compositions are provided for the treatment of disorders in a subject, such as hypertension, congestive heart failure, angina pectoris, lower urinary tract dysfunction and prostatic hypertrophy. The compositions when administered to a subject produce an α-adrenergic blocking action and contain as an active ingredient sulfamoyl-substituted phenethylamine derivatives, such as optically active 5-2-[2-(2-ethoxyphenoxy)ethylamino]-2-methylethyl-2-methoxybenzenesulfonamide, and a pharmaceutically acceptable carrier.

2 Claims, No Drawings

SULFAMOYL-SUBSTITUTED PHENETHYLAMINE DERIVATIVES, THEIR PREPARATION, AND PHARMACEUTICAL COMPOSITIONS, CONTAINING THEM

RELATED APPLICATIONS

This application is a divisional of application Ser. No. 08/174,608 filed Dec. 28, 1993, now U.S. Pat. No. 5,391,825 which is a divisional of application Ser. No. 08/068,595 filed May 28, 1993, now abandoned, which is a continuation of application Ser. No. 07/847,842, filed Mar. 9, 1992, now abandoned, which in turn is a continuation of U.S. Ser. No. 07/658,109, filed Feb. 20, 1991, now abandoned, which is a divisional of U.S. Ser. No. 07/425,708, filed Oct. 23, 1989, now abandoned, which is a continuation-in-part of Ser. No. 07/294,924, filed Jan. 5, 1989, now abandoned, which is a continuation of Ser. No. 07/105,459, filed Oct. 2, 1987, now abandoned, which in turn is a continuation of Ser. No. 06/828,063, filed Feb. 10, 1986, now abandoned, which in turn is a divisional of U.S. Ser. No. 06/803,204, filed Nov. 27, 1985, now U.S. Pat. No. 4,731,478 which is a continuation-in-part of Ser. No. 06/756,790, filed Jul. 18, 1985, now U.S. Pat. No. 4,703,063 which is a continuation of Ser. No. 06/632,258, filed Jul. 18, 1984, now U.S. Pat. No. 4,558,156, which is a continuation of Ser. No. 06/403,006, filed Jul. 29, 1982, which is abandoned and which is a divisional of Ser. No. 06/231,421, filed Feb. 4, 1981 now U.S. Pat. No. 4,373,106.

This invention relates to sulfamoyl-substituted phenethylamine derivatives and acid addition salts thereof, their preparation, and their pharmaceutical use. Compounds according to the invention exhibit α-adrenergic blocking action and can be used as antihypertensive agents and for treating congestive heart failure.

British Patent No. 2,006,772 discloses a series of compounds exhibiting α- and β-adrenergic blocking actions and that the compound shown by the following formula exhibits strong α- and β-adrenergic blocking actions

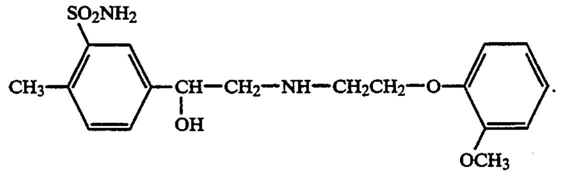

U.S. Pat. No. 3,860,647 discloses a series of compounds shown by the following general formula

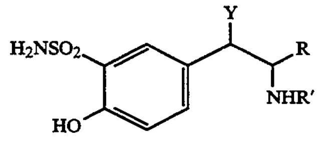

wherein R represents hydrogen or alkyl having 1–4 carbon atoms; R' represents alkyl having 1–6 carbon atoms, cycloalkyl having 3–6 carbon atoms, $XC_6H_4(CH_2)_2CH(CH_3)$, $XC_6H_4(CH_2)_2C(CH_3)_2$, $XC_6H_4CH_2CH(CH_3)$, or $XC_6H_4CH_2C(CH_3)_2$ (wherein X represents hydrogen, hydroxyl or methoxy); and Y represents hydrogen or hydroxy. It is disclosed in this U.S. Patent that these compounds exhibit β-adrenergic blocking action.

British Patent No. 902,617 discloses a series of compounds shown by the following general formula

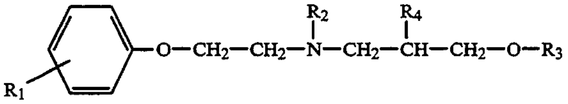

wherein $R_1$ is hydroxyl, methyl, methoxy, etc.; $R_2$ is hydrogen, methyl, etc.; $R_3$ is phenyl, benzyl or a hydroxy-, methyl-, methoxy-, ethoxy-, chloro- or bromo-substituted phenyl or benzyl radical, etc.; and $R_4$ is hydrogen, etc. These compounds exhibit α-adrenergic blocking action (see, "J. Med. Chem."; 9, 812–818(1966)) and possess antihypertensive activity.

Also, in "J. Med. Chem."; 9, 812–818(1966), it is disclosed that the phenoxyethylamine-type compounds shown by the following general formula possess α-adrenergic blocking action

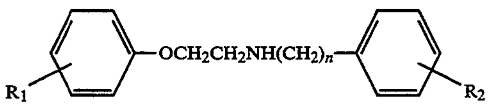

wherein $R_1$ represents o-$OCH_3$, etc., and $R_2$ represents o- or p-$OCH_3$, etc.

According to this invention there are provided sulfamoyl-substituted phenethylamine derivatives shown by following general formula I:

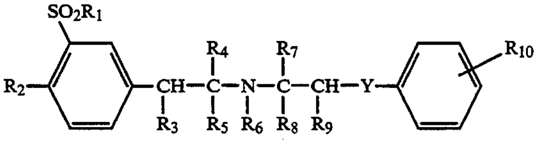

I wherein $R_1$ represents an amino group or a mono- or di-lower alkylamino group; $R_2$ represents a hydroxyl group, a lower alkyl group, or a lower alkoxy group; $R_3$ represents hydrogen, halogen, a lower alkyl group, a lower alkoxy group, a phenylthio group, or a phenylsulfinyl group; $R_4$, $R_5$, $R_6$, $R_7$, $R_8$ and $R_9$ are selected independently from hydrogen and lower alkyl groups; $R_{10}$ represents hydrogen, a lower alkyl group, or a lower alkoxy group; and Y represents oxygen or a methylene group and is oxygen when $R_2$ is a hydroxyl group; and acid addition salts thereof.

The term "lower" used herein means a straight or branched carbon chain having 1 to 5 carbon atoms. For example, "lower alkyl group" includes methyl, ethyl, propyl, butyl, pentyl and isobutyl groups, etc.; and "lower alkoxy group" includes methoxy, ethoxy, propoxy and butoxy groups, etc. Also, in the above-described formula, $R_{10}$ which is a substituent of the benzene ring may be disposed at any position ortho-, meta- or para- to the side chain. Furthermore, since the compounds of this invention shown by formula I can readily form salts and contain asymmetric carbon atoms(s), the invention includes the salts thereof, and any optically active or inactive isomer or isomer mixture thereof.

The compounds of the present invention exhibit α-adrenergic blocking action and thus can be utilized for various treatments. For example, they can be used for the treatment of hypertension, congestive heart failure, angina pectoris, lower urinary tract dysfunction, prostatic hypertrophy, pheochromocytoma and peripheral vascular disorders.

The compounds of this invention shown by formula I can be produced by the following processes.

Process 1

The compound of formula I is obtainable by reacting a compound shown by general formula II

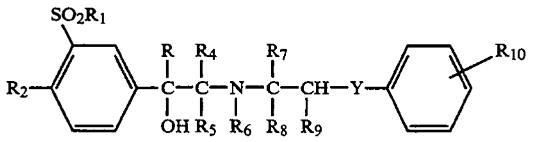

II wherein R represents hydrogen or a lower alkyl group and $R_1$, $R_2$, $R_4$, $R_5$, $R_6$, $R_7$, $R_8$, $R_9$, $R_{10}$ and Y have the same significance as in formula I with halogenating agent and then, if desired, (a) reducing the halogenated product obtained by the above reaction; or (b) reacting the halogenated product with alkaline material and then reacting the product thus obtained with hydrogen iodide, a lower alcohol, or thiophenol, and further, if desired, oxidizing the product obtained by the reaction with thiophenol.

In process I a starting material shown by formula II described above can be reacted with halogenating agent to provide a product shown by general formula $I_1$

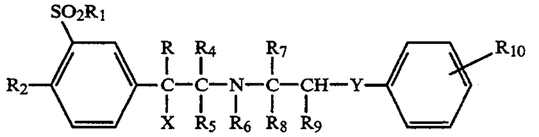

$I_1$ wherein X represents chlorine or bromine and R, $R_1$, $R_2$, $R_4$, $R_5$, $R_6$, $R_7$, $R_8$, $R_9$, $R_{10}$ and Y have the same significance as in formula II and then, if desired, (a) the halogenated product shown by formula $I_1$ is reduced to form a compound shown by formula $I_2$

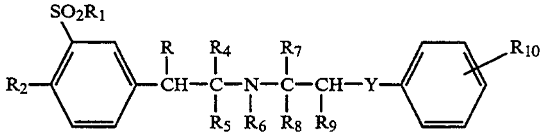

$I_2$ wherein R, $R_1$, $R_2$, $R_4$, $R_5$, $R_6$, $R_7$, $R_8$, $R_9$, $R_{10}$ and Y have the same significance as above described; or (b) the halogenated product shown by formula $I_1$ is treated with alkaline material to form the aziridine compound shown by following general formula III

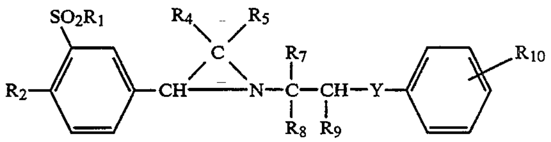

III wherein $R_1$, $R_2$, $R_4$, $R_5$, $R_7$, $R_8$, $R_9$, $R_{10}$ and Y have the same significance as above described, and then the aziridine compound is reacted with hydrogen iodide, a lower alcohol, or thiophenol to provide the compound shown by general formula $I_3$

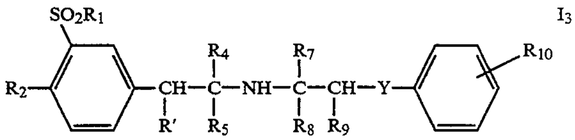

$I_3$ wherein R′ represents iodine, a lower alkoxy group or a phenylthio group and $R_1$, $R_2$, $R_4$, $R_5$, $R_7$, $R_8$, $R_9$, $R_{10}$ and Y have the same significance as above described; further, when R′ of the compound shown by formula $I_3$ is a phenylthio group the compound can be oxidized to provide the compound shown by general formula $I_4$

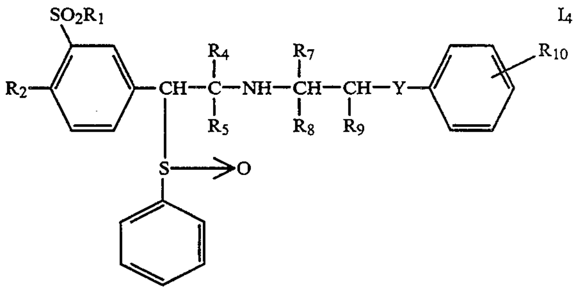

$I_4$ wherein $R_1$, $R_2$, $R_4$, $R_5$, $R_7$, $R_8$, $R_9$, $R_{10}$ and Y have the same significance as above described.

This process is further schematically shown below, the compounds shown by formulae $I_1$, $I_2$, $I_3$ and $I_4$ being compounds according to this invention.

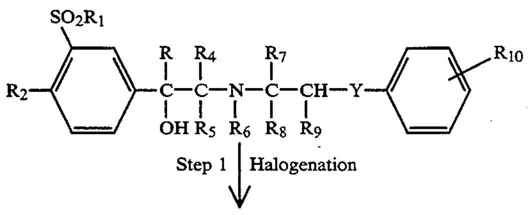

II

-continued

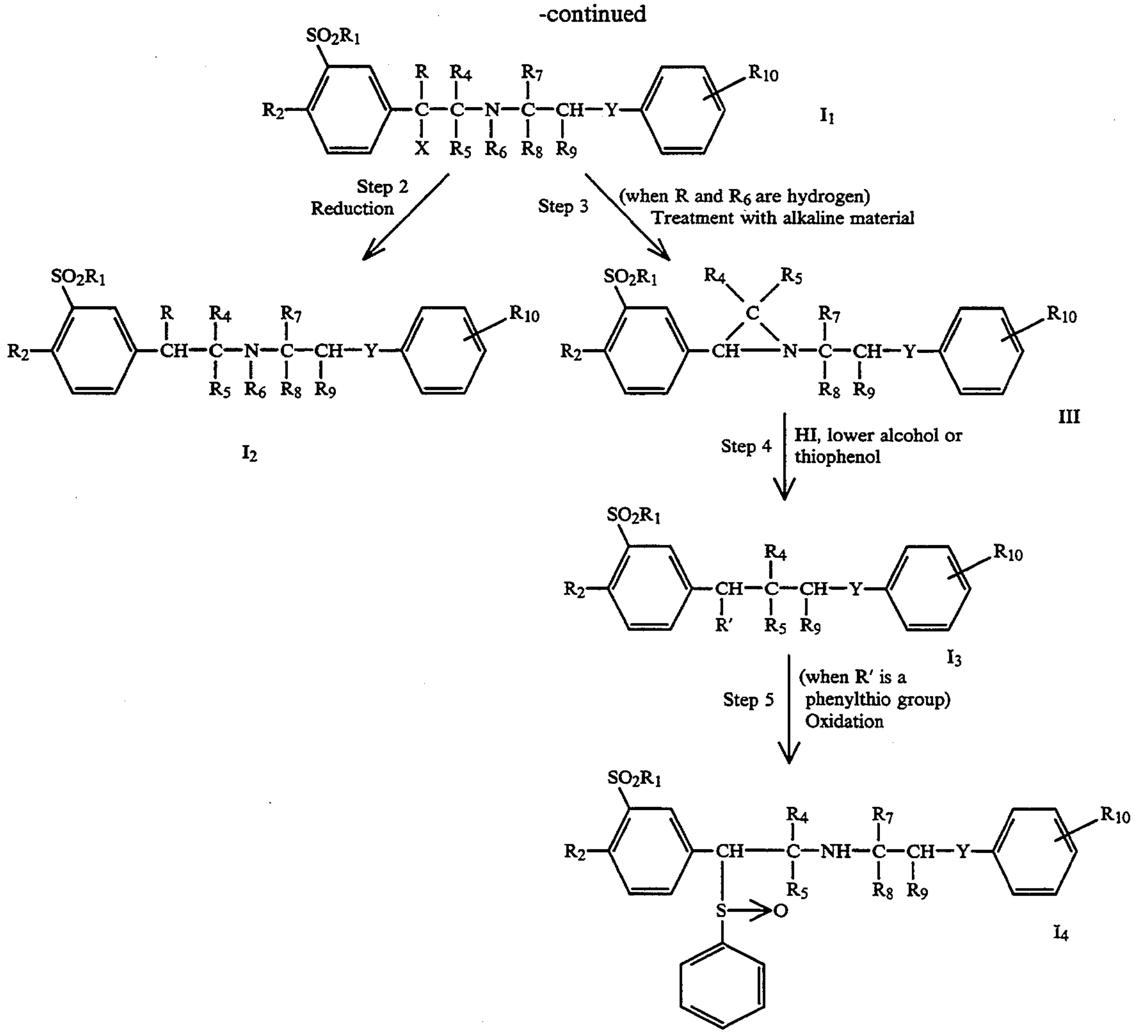

The reaction conditions in the steps described above may be as follows:

Step 1: The halogenation of the compounds of formula II can be performed in an organic solvent such as toluene, methyl ethyl ketone, acetonitrile, tetrahydrofuran, etc., at room temperature or under heating using a halogenating agent such as thionyl chloride, hydrogen chloride, hydrogen bromide, phosphorus trichloride, phosphorus pentachloride, phosphorus oxychloride, thionyl bromide, etc.

Step 2: The reduction of the compounds of formula $I_1$ can be performed in an organic solvent such as methanol, ethanol, toluene, acetonitrile, tetrahydrofuran, etc., under hydrogen stream, at normal temperature and normal pressure using a catalyst such as platinum oxide, palladium carbon, etc.

Step 3: The compounds of formula III can be obtained by treating the compounds of formula $I_1$ (wherein, however, R and $R_6$ are hydrogen) with an alkaline material such as sodium carbonate, metal alcoholate, sodium hydroxide, potassium hydroxide, etc., in an organic solvent such as ethyl acetate, ethanol, dioxane, benzene, etc., at room temperature to 50° C.

Step 4:

i): The compounds of formula $I_3$ (wherein R' is a phenylthio group) can be obtained by reacting the compounds of formula III with thiophenol in an organic solvent such as methanol, chloroform, ethyl acetate, dioxane, benzene, etc., at room temperature.

ii): The compounds of formula $I_3$ (wherein R' is a lower alkoxy group) can be obtained by reacting the compounds of formula III with a lower alcohol in the presence of $BF_3$ catalyst under the same condition as in the step i).

iii): The compounds of formula $I_3$ (wherein R' is iodine) can be obtained by reacting the compounds of formula III with hydroiodic acid in an organic solvent such as dioxane, methanol, etc., at room temperature.

Step 5: The oxidation of the compounds of formula $I_3$ (wherein R' is a phenylthio group) can be performed in acetic acid at temperatures of 50°–60° C. using $H_2O_2$ as the oxidizing agent.

In addition, among the compounds of this invention, the compounds shown by following general formula $I_5$

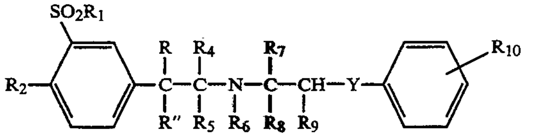

$I_5$ wherein R" represents a lower alkoxy group or a phenylthio group and R, $R_1$, $R_2$, $R_4$, $R_5$, $R_6$, $R_7$, $R_8$, $R_9$, $R_{10}$ and Y have the same significance as above described can be obtained by reacting the compounds of formula $I_1$ directly with a lower alcohol or thiophenol.

The starting materials of formula II wherein R is hydrogen used in the process of this invention are described in British Patent No. 2,006,772; the starting materials of formula II wherein R is a lower alkyl group can be obtained by reacting the compounds of the following formula

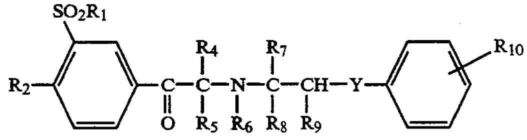

described in the aforesaid British patent with a Grignard reagent (lower alkyl-MgX).

Process 2

A compounds of this invention shown by following general formula $I_6$

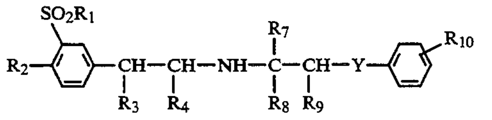

$I_6$ wherein $R_1$, $R_2$, $R_3$, $R_4$, $R_7$, $R_8$, $R_9$, $R_{10}$ and Y have the same significance as in formula I can be produced by condensing the compounds shown by the general formulae

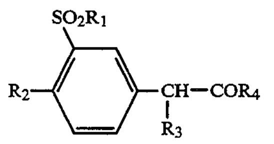

IV and

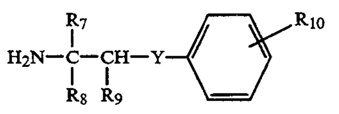

V and then reducing the product thus obtained.

This reaction is performed by condensing the compounds of formulae IV and V in an organic solvent such as methanol, ethanol, toluene, acetonitrile, tetrahydrofuran, etc., and then reducing the product, e.g. in the presence of $PtO_2$ catalyst or Raney nickel catalyst or with $NaBH_4$, $LiAlH_4$, etc.

The isolation and purification of the compounds of this invention shown by general formulae $I_1$–$I_6$ and formed by Process I or 2 may be effected by filtration, extraction with a solvent, separation by column chromatography, recrystallization, etc.

The pharmacological effects of compounds of this invention were determined by the following experiments. The effects of compounds of this invention were compared with those of 5-{1-hydroxy-2-[2-(2-methoxyphenoxy)ethylamino]ethyl}-2-methylbenzenesulfonamide (Compound A, which is one of the typical compounds presented in British Patent No. 2,006,772 and of phentolamine.

A. α-Adrenergic blocking action

The blood pressure was measured in rats anesthetized with urethane and treated with pentolinium. The effects of the test samples (intravenous injection—i.v.) on the hypertensive response to phenylephrine (10 μg/Kg i.v.) were measured and the results are shown in Table I.

B. Antihypertensive effects in spontaneously hypertensive rats

Oral administration (p.o.): The systolic blood pressure of spontaneously hypertensive rats having systolic blood pressure higher than 150 mmHg was measured indirectly by the tail cuff method using a programmed electrosphygmanometer (Narco Bio-Systems Inc. PE-300), the results being shown in Table II.

TABLE I

Adrenergic blocking action:

| Sample | α-adrenergic blocking $ED_{50}$ (mg/Kg) i.v. |
|---|---|
| Compounds of this invention (Ex. No.) | |
| 4 | 0.00035 |
| 5 | 0.00026 |
| 10 | 0.0059 |
| 11 | 0.012 |
| 12 | 0.0073 |
| 15 | 0.0013 |
| 16 | 0.0008 |
| 20 | 0.00000014 |
| 25 | 0.0012 |
| 26 | 0.004 |
| Known compounds | |
| Compound A | 0.034 |
| Phentolamine | 0.061 |

TABLE II

Antihypertensive effect:

| Sample | Dose (mg/Kg) | Change in systolic blood pressure (mmHg) at stated dose p.o. |
|---|---|---|
| Compounds of this invention (Ex. No.) | | |
| 10 | 10 | −57 ± 5.6 |
| 11 | 30 | −50 ± 4.7 |
| 12 | 10 | −48 ± 2.0 |
| 15 | 10 | −54 ± 6.2 |
| 16 | 10 | −71 ± 11.1 |
| 20 | 3 | −57 ± 4.2 |
| 25 | 10 | −46 ± 3.6 |
| 26 | 10 | −46 ± 4.3 |
| Known compounds | | |
| Compound A | 10 | −35 ± 6.4 |
| Phentolamine | 10 | +7.8 ± 5.0 |
| " | 100 | −70 ± 10.1 |

The clinical administration of the compounds of this invention to a subject or host, such as a human being, is usually practiced by intravenous injection or orally as the free bases or the acid addition salts thereof (e.g. hydrochlorides, sulfates, maleates, acetates, furarates, lactates, citrates, etc.). It is appropriate to administer 10 ng–1 mg doses of the compound several times per day in the case of intravenous administration, or 0.1–100 mg of the compounds two or three times per day in the case of oral administration.

The compounds of this invention may be formulated into ordinary dosage forms such as, for example, tablets, capsules, pills, solutions, etc., and these medicaments can be prepared by conventional methods using usual medical excipients and pharmaceutically acceptable carriers.

The production of compounds of this invention is illustrated in the following Examples.

In addition, the raw materials used in this invention include novel compounds and the production thereof is shown in Reference Examples.

REFERENCE EXAMPLE 1

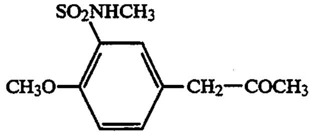

(1) To 250 g of chlorosulfonic acid was added dropwise 50 g of 4-methoxyphenylacetone at 0°–5° C. After stirring the mixture for 4 hours at room temperature, the reaction mixture was poured into 2,500 ml of ice water and extracted thrice with 500 ml of ethyl acetate. The extract was washed with water and after drying the extract with anhydrous magnesium sulfate, the solvent was distilled off under reduced pressure. The crude crystals obtained were recrystallized from benzene-ether to provide 32 g of 3-chlorosulfonyl-4-methoxyphenylacetone.

Melting point: 80°–81° C.

(2) In 26 ml of tetrahydrofuran was dissolved 2.6 g of 3-chlorosulfonyl-4-methoxyphenylacetone and then 1.2 g of 40% methylamine was added dropwise to the solution at a temperature lower than 10° C. After stirring the mixture for one hour at room temperature, the solvent was distilled off under reduced pressure and the residue was extracted with ethyl acetate. The extract was washed with water and after drying with anhydrous magnesium sulfate, the solvent was distilled off under reduced pressure. The crude crystals obtained were recrystallized from isopropanol-ether to provide 1.8 g of 4-methoxy-3-N-methylsulfamylphenylacetone.

Melting point: 100°–101° C.

REFERENCE EXAMPLE 2

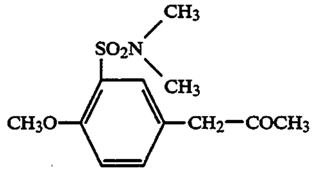

By reacting 2.6 g of 3-chlorosulfonyl-4-methoxyphenylacetone and 0.6 g of dimethylamine in the same manner as in Reference example 1-(2), 2.5 g of oily 4-methoxy-3-N,N-dimethylsulfamylphenylacetone was obtained.

Nuclear magnetic resonance spectra ($CDCl_3$): δ: 2.18 (3H, S, $COCH_3$) 2.82 (6H, S, $N(CH_3)_2$) 3.69 (2H, S,

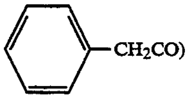

3.90 (3H, S, O—$CH_3$)

EXAMPLE 1

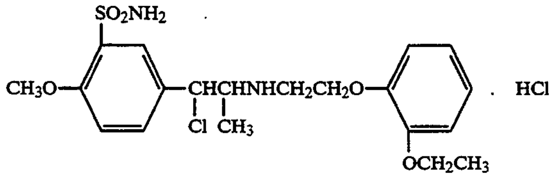

In 1,000 ml of acetonitrile was suspended 17 g of 5-{2-[2-(2-ethoxyphenoxy)ethylamino]-1-hydroxy-2-methylethyl}-2-methoxybenzenesulfonamide hydrochloride and while stirring the suspension, 9 g of thionyl chloride was added dropwise to the suspension at room temperature, whereby the product first dissolved and then began to crystallize gradually. After stirring the mixture for two days, the crystals formed were recovered by filtration, washed with chloroform and dried to provide 15 g of 5-{1-chloro-2-[2-(2-ethoxyphenoxy)ethylamino]-2-methylethyl}-2-methoxybenzenesulfonamide hydrochloride.

The product has the following physicochemical properties:

Melting point: 197°–200° C.

| Elemental analysis for $C_{20}H_{27}N_2O_5SCl.HCl$: | C (%) | H (%) | N (%) |
|---|---|---|---|
| Calcd.: | 50.11 | 5.89 | 5.84 |
| Found: | 50.06 | 5.96 | 5.95 |

Nuclear magnetic resonance spectra ($CD_3OD$): δ: 1.30 (3H, d, CH—$CH_3$) 1.40 (3H, t, $CH_2$—$CH_3$) 3.63 (2H, t, $CH_2$—$CH_2$—N) 4.01 (3H, s, O—$CH_3$) 4.12 (2H, q, $CH_3$—$CH_2$—O) 4.36 (2H, t, $CH_2$—$CH_2$—O) 5.30 (1H, d, Cl—CH)

The compounds in Examples 2 and 3 were obtained in the same manner as in Example 1.

EXAMPLE 2

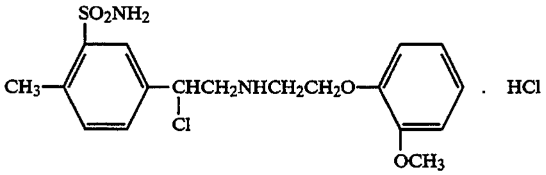

5-{1-Chloro-2-[2-(2-methoxyphenoxy)ethylamino]ethyl}-2-methylbenzenesulfonamide hydrochloride Physicochemical properties:

Melting point: 190°–191° C.

| Elemental analysis for $C_{18}H_{23}N_2O_4SCl.HCl$: | C (%) | H (%) | N (%) |
|---|---|---|---|
| Calculated: | 49.66 | 5.56 | 6.43 |
| Found: | 49.51 | 5.70 | 6.53 |

Nuclear magnetic resonance spectra ($d_6$-DMSO): δ: 2.61 (3H, s,

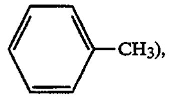

3.64 (3H, s,

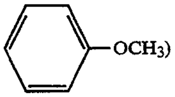

5.66 (1H, m,

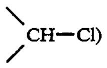

EXAMPLE 3

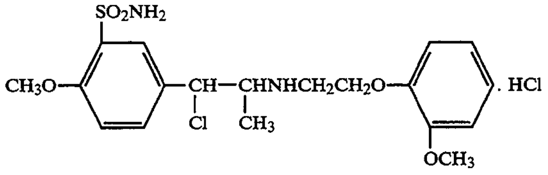

5-{1-Chloro-2-[2-(2-methoxyphenoxy)ethylamino]-2-methylethyl}-2-methoxybenzenesulfonamide hydrochloride Physicochemical properties:

Melting point: 195°-197° C. (decomposed)

| Elemental analysis for $C_{19}H_{25}N_2O_5SCl.HCl$: | C (%) | H (%) | N (%) |
|---|---|---|---|
| Calculated: | 49.04 | 5.63 | 6.02 |
| Found: | 49.02 | 5.64 | 6.08 |

Nuclear magnetic resonance spectra ($CD_3OD+d_6$-DMSO): δ: 1.18 (3H, d,

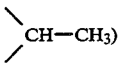

3.80 and 3.95 (3H+3H, s, —O—$CH_3$) 5.56 (1H, d,

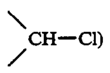

EXAMPLE 4

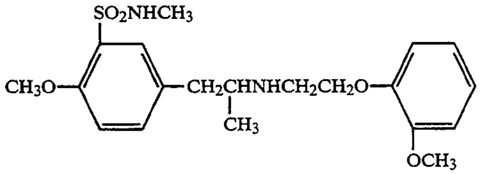

A mixture of 1.4 g of 4-methoxy-3-N-methylsulfamylphenylacetone, 1 g of 2-methoxyphenoxyethylamine, and 30 ml of methanol was refluxed for one hour. After cooling the mixture, 60 mg of a platinum oxide catalyst was added thereto, and reduction was performed at normal temperature and pressure. After absorption of a theoretical amount of hydrogen, the catalyst was filtered away. After the filtrate was acidified with alcoholic 5% hydrochloric acid, the solvent was distilled off under reduced pressure to form 1.6 g of crystals, which were recovered and recrystallized to provide 1.2 g of the colorless crystals of 2-methoxy-5-{2-[2-(2-methoxyphenoxy)ethylamino]-2-methylethyl}-N-methylbenzenesulfonamide hydrochloride.

The product has the following physicochemical properties:

Melting point: 162°-163° C.

| Elemental analysis for $C_{20}H_{28}N_2O_5S.HCl$: | C (%) | H (%) | N (%) |
|---|---|---|---|
| Calcd.: | 53.99 | 6.57 | 6.30 |
| Found: | 53.85 | 6.70 | 6.27 |

Nuclear magnetic resonance spectra ($d_6$-DMSO): δ: 1.15 (3H, d, —$CHCH_3$) 3.76 and 3.88 (3H+3H, S, O—$CH_3$)

The compound of Example 5 was obtained in the same manner as in Example 4.

EXAMPLE 5

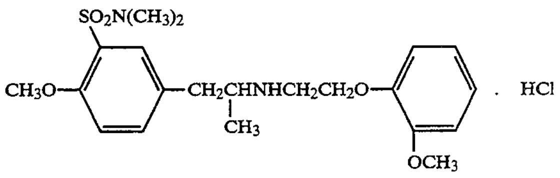

2-Methoxy-5-{2-[2-(2-methoxyphenoxy)ethylamino]-2-methylethyl}-N,N-dimethylbenzenesulfonamide hydrochloride Physicochemical properties:

Melting point: 185°-187° C.

| Elemental analysis for $C_{21}H_{30}N_2O_5S.HCl$: | C (%) | H (%) | N (%) |
|---|---|---|---|
| Calculated: | 54.95 | 6.81 | 6.10 |
| Found: | 54.73 | 6.88 | 5.85 |

Nuclear magnetic resonance spectra ($d_6$-DMSO): δ: 1.16 (3H, d, $CHCH_3$), 2.71 (6H, s, $N(CH_3)_2$) 3.76 and 3.87 (3H+3H, s, —O—$CH_3$)

REFERENCE EXAMPLE 3

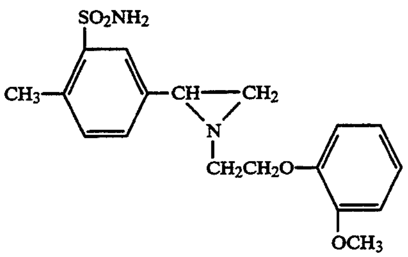

In 50 ml of ethyl acetate was suspended 4.35 g (0.01 mole) of 5-{1-chloro-2-[2-(2-methoxyphenoxy)ethylamino]ethyl}-2-methylbenzenesulfonamide hydrochloride and then 50 ml of an aqueous 10% sodium carbonate solution was added to the suspension with stirring. After further stirring overnight vigorously, the reaction mixture was recovered by decantation. After removing inorganic matter by passing the ethyl acetate layer thus recovered through a silica gel column (50 ml of silica gel), the reaction product was evaporated to dryness to provide 3.2 g (88%) of colorless resinous 5-{1-[2-(2-methoxyphenoxy)ethyl]aziridin-2-yl}-2-methylbenzenesulfonamide.

The product has the following physicochemical properties:

Amorphous form.

| Elemental analysis for $C_{18}H_{22}N_2O_4S$: | C (%) | H (%) | N (%) |
|---|---|---|---|
| Calcd.: | 59.65 | 6.12 | 7.73 |
| Found: | 59.37 | 6.12 | 7.61 |

Nuclear magnetic resonance spectra ($CDCl_3$): δ: 1.74 and 1.95 (1H+1H, d,

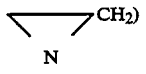

2.43 (1H, q,

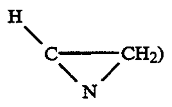

2.55 (3H, s,

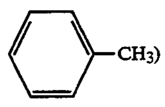

4.10 (2H, t, O—$CH_2$—)

EXAMPLE 6

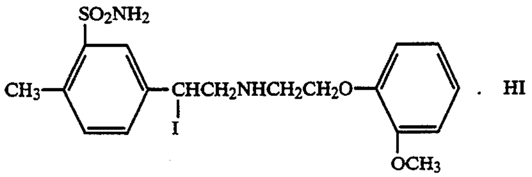

In 50 ml of dioxane was dissolved 2.5 g of 5-{1-[2-(2-methoxyphenoxy)ethyl]aziridin-2-yl}-2-methylbenzenesulfonamide and after adding thereto 1 g of concentrated hydroiodic acid, the mixture was stirred overnight. After the reaction was over, the solvent was distilled off under reduced pressure and the residue was washed thrice with 30 ml of water and then thrice with 200 ml of ether and crystallized by the addition of ethyl acetate. The crystals were recovered by filtration, washed with water, and dried to provide 1.7 g of 5-{1-iodo-2-[2-(2-methoxyphenoxy)ethylamino]ethyl}-2-methylbenzenesulfonamide hydroiodide.

The product has the following physicochemical properties:

Melting point: 154°-155° C.

| Elemental analysis for $C_{18}H_{23}N_2O_4SI.HI$: | C (%) | H (%) | N (%) |
|---|---|---|---|
| Calcd.: | 34.97 | 3.91 | 4.53 |
| Found: | 35.07 | 3.98 | 4.39 |

Nuclear magnetic resonance spectra ($CD_3OD$): δ: 2.65 (3H, s,

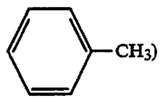

3.54 (2H, t, —$CH_2$—N—) 4.30 (2H, t, —$CH_2$—O) 5.55 (1H, t,

EXAMPLE 7

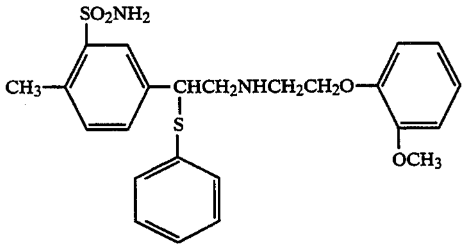

In 50 ml of methanol was dissolved 2.5 g of 5-{1-[2-(2-methoxyphenoxy)ethyl]aziridin-2-yl}-2-methylbenzenesulfonamide and after adding 1 g of thiophenol to the solution and stirring the mixture overnight at room temperature, methanol was distilled off. The residue was subjected to silica gel column chromatography and the product was eluted by a mixed solvent of chloroform and methanol (9:1 by volume ratio) to provide 2.4 g of 5-{2-[2-(2-methoxyphenoxy)ethylamino]-1-phenylthioethyl}-2-methylbenzenesulfonamide as a viscous oily material.

The product has the following physicochemical properties:

Amorphous form.

| Elemental analysis for $C_{24}H_{28}N_2O_4S_2$: | C (%) | H (%) | N (%) |
|---|---|---|---|
| Calcd.: | 60.99 | 5.97 | 5.93 |
| Found: | 60.72 | 6.11 | 5.71 |

Nuclear magnetic resonance spectra ($CDCl_3$): δ: 2.58 (3H, s,

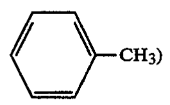

3.74 (3H, s, O—$CH_3$) 3.98 (2H, t, —$CH_2$—O) 4.35 (1H, t,

EXAMPLE 8

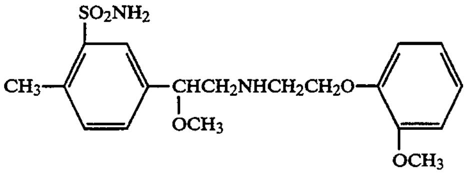

In 50 ml of methanol was dissolved 2.5 g of 5-{1-[2-(2-methoxyphenoxy)ethyl]aziridin-2-yl}-2-methylbenzenesulfonamide and after adding thereto 2 ml of a boron trifluoride ether complex at room temperature, the mixture was stirred overnight. Thereafter, methanol was distilled off under reduced pressure and the residue was subjected to silica gel column chromatography and eluted with a mixed solvent of chloroform and methanol (9:1 by volume ratio), whereby 1.5 g of a colorless viscous oily material was obtained. The product was crystallized by the addition of 5 ml of methanol and several drops of ammonia. The crystals formed were recovered by filtration, washed with water, and dried to provide 1.2 g of 5-{1-methoxy-2-[2-(2-methoxyphenoxy)ethylamino]ethyl}-2-methylbenzenesulfonamide.

The product has the following physicochemical properties:

Melting point: 150°-152° C.

| Elemental analysis for $C_{19}H_{26}N_2O_5S$: | C (%) | H (%) | N (%) |
|---|---|---|---|
| Calcd.: | 57.85 | 6.64 | 7.10 |
| Found: | 57.58 | 6.79 | 7.24 |

Nuclear magnetic resonance spectra ($CD_3OD$): δ: 2.65 (3H, s,

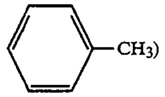

2.98 (2H, t, —$CH_2$N) 3.80 (3H, s,

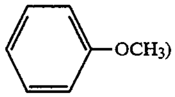

3.26 (3H, s, CH—$OCH_3$) 4.10 (2H, t, —$CH_2$O) 4.40 (1H, q,

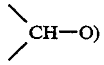

EXAMPLE 9

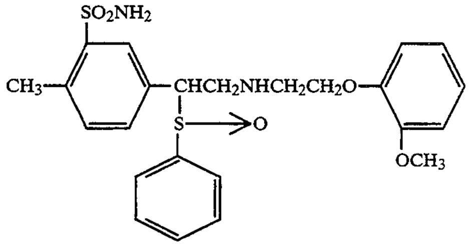

In 20 ml of acetic acid was dissolved 2 g of 5-{2-[2-(2-methoxyphenoxy)ethylamino]-1-phenylthioethyl}-2-methylbenzenesulfonamide and after adding thereto 0.5 ml of 30% $H_2O_2$, the mixture was heated to 50°-60° C. for 3 hours. After adding thereto 100 ml of water, the reaction mixture was extracted with 200 ml of ethyl acetate. The ethyl acetate extract was washed with an aqueous 1% sodium carbonate solution and then ethyl acetate was distilled off under reduced pressure. The residue was subjected to silica gel column chromatography, the product was eluted with a mixed solvent of chloroform and methanol (9:1 by volume ratio), and the colorless viscous oily product thus obtained was crystallized by the addition of ethyl acetate. The crystals formed were recovered by filtration to provide 1.3 g of 5-{2-[2-(2-methoxyphenoxy)ethylamino]-1-phenylsulfinylethyl}-2-methylbenzenesulfonamide.

The product has the following physicochemical properties:

Melting point: 139°-141° C.

| Elemental analysis for $C_{24}H_{28}N_2O_5S_2$: | C (%) | H (%) | N (%) |
|---|---|---|---|
| Calcd.: | 59.00 | 5.78 | 5.73 |
| Found: | 58.91 | 5.74 | 5.72 |

EXAMPLE 10

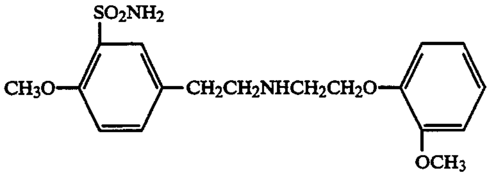

In 150 ml of methanol was dissolved 3.8 g of 5-{1-chloro-2-[2-(2-methoxyphenoxy)ethylamino]ethyl}-2-methoxybenzenesulfonamide hydrochloride and after adding thereto 0.5 g of 10% palladium carbon, dechlorination was performed under hydrogen stream at normal temperature and pressure. The palladium carbon was filtered away and the filtrate was concentrated under reduced pressure to provide 3.1 g of 2-methoxy-5-{2-[2-(2-methoxyphenoxy)ethylamino]ethyl}benzenesulfonamide hydrochloride, which was recrystallized from 120 ml of a mixture of methanol and ethanol (1:4 by volume ratio) to provide 2.3 g of the colorless crystals thereof.

The product has the following physicochemical properties:

Melting point: 196°-198° C.

| Elemental analysis for $C_{18}H_{24}N_2O_5S.HCl$): | C (%) | H (%) | N (%) |
|---|---|---|---|
| Calcd.: | 51.86 | 6.04 | 6.72 |
| Found: | 51.72 | 6.23 | 6.68 |

Nuclear magnetic resonance spectra ($CD_3OD$): δ: 3.84 and 3.98 (3H+3H, s, —$OCH_3$) 4.24 (2H, t, —$OCH_2$—)

The compounds in Examples 11-29 were obtained in the same manner as in Example 10.

EXAMPLE 11

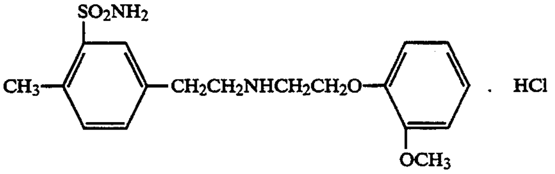

5-{2-[2-(2-Methoxyphenoxy)ethylamino]ethyl}-2-methylbenzenesulfonamide hydrochloride Physicochemical properties:

Melting point: 173°-175° C.

| Elemental analysis for $C_{18}H_{24}N_2O_4S.HCl$: | C (%) | H (%) | N (%) |
|---|---|---|---|
| Calculated: | 53.93 | 6.28 | 6.99 |
| Found: | 53.83 | 6.27 | 6.97 |

)

Nuclear magnetic resonance spectra ($CD_3OD$): δ: 2.64 (3H, s,

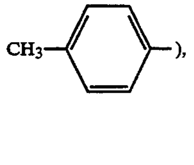

3.84 (3H, s, —$OCH_3$) 4.28 (2H, t, —$OCH_2$—)

EXAMPLE 12

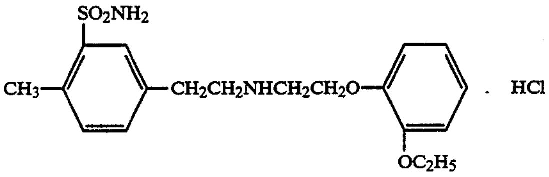

5-{2-[2-(2-Ethoxyphenoxy)ethylamino]ethyl}-2-methylbenzenesulfonamide hydrochloride Physicochemical properties:

Melting point: 180°-181.5° C.

| Elemental analysis for $C_{19}H_{26}N_2O_4S.HCl$: | C (%) | H (%) | N (%) |
|---|---|---|---|
| Calculated: | 55.00 | 6.56 | 6.75 |
| Found: | 54.81 | 6.56 | 6.89 |

Nuclear magnetic resonance spectra ($CD_3OD$): δ: 1.36 (3H, t, —$OCH_2CH_3$), 2.64 (3H, s,

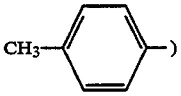

4.10 (2H, q, —$OCH_2CH_3$), 4.36 (2H, t, —$OCH_2$—$CH_2$—)

EXAMPLE 13

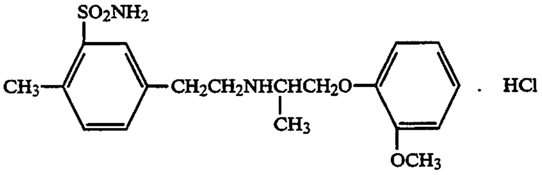

5-{2-[2-(2-Methoxyphenoxy)-1-methylethylamino]ethyl}-2-methylbenzenesulfonamide hydrochloride Physicochemical properties:

Melting point: 169°-171° C.

| Elemental analysis for $C_{19}H_{26}N_2O_4S.HCl$: | C (%) | H (%) | N (%) |
|---|---|---|---|
| Calculated: | 55.00 | 6.56 | 6.75 |
| Found: | 54.89 | 6.60 | 6.76 |

Nuclear magnetic resonance spectra ($CD_3OD$): δ: 1.15 (3H, d,

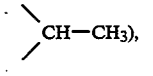 2.64 (3H, s, 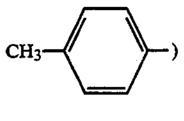

3.80 (3H, s, —$OCH_3$)

EXAMPLE 14

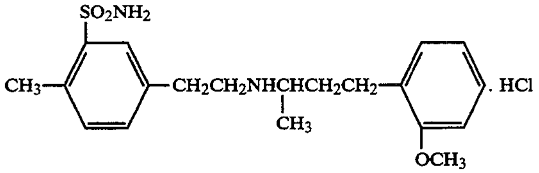

5-{2-[3-(2-Methoxyphenyl)-1-methylpropylamino]ethyl}-2-methylbenzenesulfonamide hydrochloride Physicochemical properties:

Melting point: 198°-200° C.

| Elemental analysis for $C_{20}H_{28}N_2O_3S.HCl$: | C (%) | H (%) | N (%) |
|---|---|---|---|
| Calculated: | 58.17 | 7.08 | 6.78 |
| Found: | 58.09 | 7.01 | 6.62 |

Nuclear magnetic resonance spectra ($d_6$-DMSO): δ: 1.35 (3H, d,

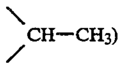

2.55 (3H, s,

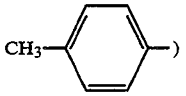

3.78 (3H, s, —$OCH_3$)

EXAMPLE 15

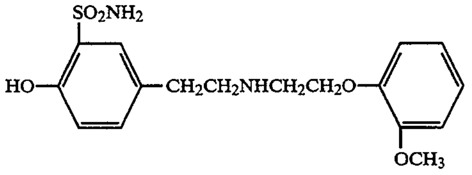

2-Hydroxy-5-{2-[2-(2-methoxyphenoxy)ethylamino]ethyl}benzenesulfonamide

Physicochemical properties:

Melting point: 97°-99° C.

| Elemental analysis for $C_{17}H_{22}N_2O_5S.H_2O$: | C (%) | H (%) | N (%) |
|---|---|---|---|
| Calculated: | 53.10 | 6.29 | 7.29 |
| Found: | 52.75 | 6.22 | 7.09 |

Nuclear magnetic resonance spectra ($d_6$-DMSO): δ: 3.76 (3H, s, —$OCH_3$) 4.04 (2H, t, —$OCH_2$—)

EXAMPLE 16

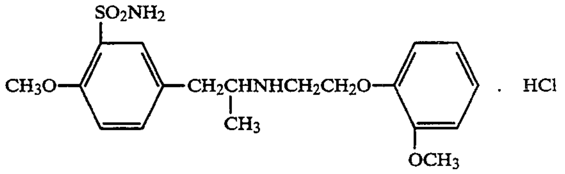

2-Methoxy-5-{2-[2-(2-methoxyphenoxy)ethylamino]-2-methylethyl}benzenesulfonamide hydrochloride Physicochemical properties:

Melting point: above 250° C.

| Elemental analysis for $C_{19}H_{26}N_2O_5S.HCl$: | C (%) | H (%) | N (%) |
|---|---|---|---|
| Calculated: | 52.96 | 6.31 | 6.50 |
| Found: | 52.44 | 6.31 | 6.47 |

Nuclear magnetic resonance spectra ($d_6$-DMSO): δ 1.15 (3H, d,

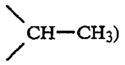

3.78 and 3.90 (3H+3H, s, —$OCH_3$) 4.38 (2H, t, —$OCH_2$—)

EXAMPLE 17

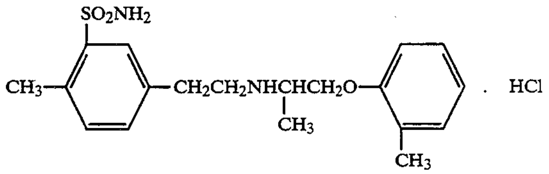

2-Methyl-5-{2-[2-(2-methylphenoxy)-1-methylethylamino]ethyl}benzenesulfonamide hydrochloride Physicochemical properties:

Melting point: 183°-185° C.

| Elemental analysis for $C_{19}H_{26}N_2O_3S.HCl$: | C (%) | H (%) | N (%) |
|---|---|---|---|
| Calculated: | 57.20 | 6.82 | 7.02 |
| Found: | 57.13 | 6.79 | 6.99 |

Nuclear magnetic resonance spectra ($CD_3OD$): δ: 1.55 (3H, d,

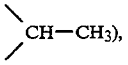

2.24 (3H, s,

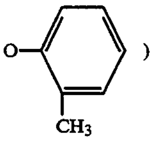

2.64 (3H, s,

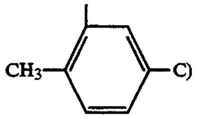

2.08-2.40 (2H, m, —$OCH_2$—)

EXAMPLE 18

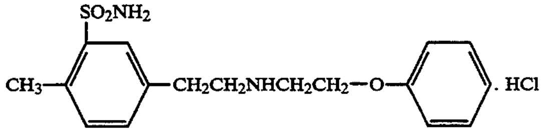

2-Methyl-5-[2-(2-phenoxyethylamino)ethyl]benzenesulfonamide hydrochloride

Physicochemical properties:

Melting point: 208.5°-210° C.

| Elemental analysis for $C_{17}H_{22}N_2O_3S.HCl$: | C (%) | H (%) | N (%) |
|---|---|---|---|
| Calculated: | 55.05 | 6.25 | 7.55 |
| Found: | 54.83 | 6.23 | 7.48 |

Nuclear magnetic resonance spectra ($CD_3OD$): δ: 2.65 (3H, s,

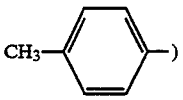

)

4.32 (2H, t, —$OCH_2$—)

EXAMPLE 19

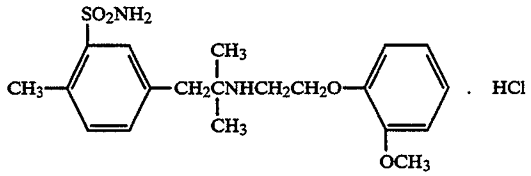

5-{2-[2-(2-Methoxyphenoxy)ethylamino]-2,2-dimethylethyl}-2-methylbenzenesulfonamide hydrochloride Physicochemical properties:

Melting point: 199°-202° C.

| Elemental analysis for $C_{20}H_{28}N_2O_4S.HCl.CH_3OH$: | C (%) | H (%) | N (%) |
|---|---|---|---|
| Calculated: | 54.71 | 7.21 | 6.08 |

-continued

| Elemental analysis for $C_{20}H_{28}N_2O_4S.HCl.CH_3OH$: | C (%) | H (%) | N (%) |
|---|---|---|---|
| Found: | 54.50 | 7.17 | 6.14 |

Nuclear magnetic resonance spectra ($d_6$-DMSO): δ: 1.24 (6H, s,

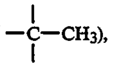

2.56 (3H, s,

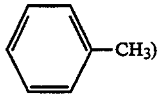

3.74 (3H, s,

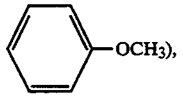

4.30 (2H, t, —$CH_2$—O)

EXAMPLE 20

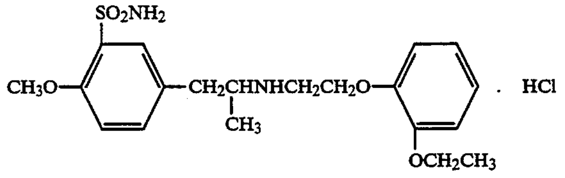

5-{2-[2-(2-Ethoxyphenoxy)ethylamino]-2-methylethyl}-2-methoxybenzenesulfonamide hydrochloride Physicochemical properties:

Melting point: 254°-256° C.

| Elemental analysis for $C_{20}H_{28}N_2O_5S.HCl$: | C (%) | H (%) | N (%) |
|---|---|---|---|
| Calculated: | 53.99 | 6.57 | 6.30 |
| Found: | 53.79 | 6.58 | 6.26 |

Nuclear magnetic resonance spectra ($CD_3OD$): δ: 1.28 (3H, d,

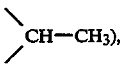

1.38 (3H, t, $CH_2$—$CH_3$) 3.97 (3H, s, O—$CH_3$), 4.30 (2H, t, $CH_2$—$CH_2$—O)

EXAMPLE 21

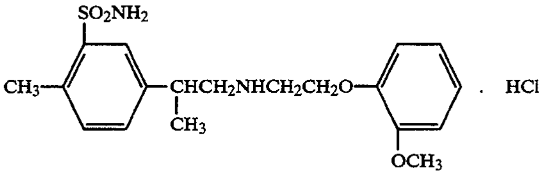

5-{2-[2-(2-Methoxyphenoxy)ethylamino]-1-methylethyl}-2-methylbenzenesulfonamide hydrochloride Physicochemical properties:

Melting point: 183°-185° C.

| Elemental analysis for $C_{19}H_{26}N_2O_4S.HCl$: | C (%) | H (%) | N (%) |
|---|---|---|---|
| Calculated: | 55.00 | 6.56 | 6.75 |
| Found: | 54.76 | 6.56 | 6.74 |

Nuclear magnetic resonance spectra ($CD_3OD$): δ: 1.40 (3H, d,

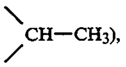 2.64 (3H, s, 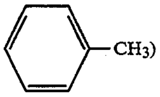

3.80 (3H, s,

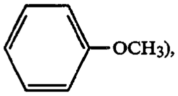

4.23 (2H, t, —$CH_2$—O)

EXAMPLE 22

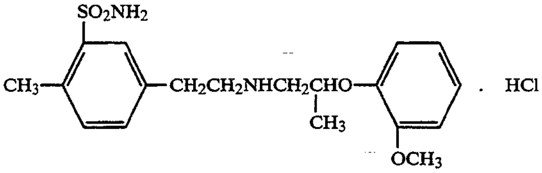

5-{2-[2-(2-Methoxyphenoxy)-2-methylethylamino]ethyl}-2-methylbenzenesulfonamide hydrochloride Physicochemical properties:

Melting point: 231°-232° C.

| Elemental analysis for $C_{19}H_{26}N_2O_4S.HCl$: | C (%) | H (%) | N (%) |
|---|---|---|---|
| Calculated: | 55.00 | 6.56 | 6.75 |
| Found: | 54.86 | 6.58 | 6.83 |

Nuclear magnetic resonance spectra ($CD_3OD$): δ: 1.26 (3H, d,

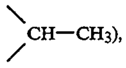 2.60 (3H, s, 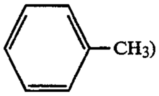

3.76 (3H, s,

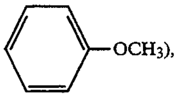

4.42 (1H, m,

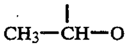

EXAMPLE 23

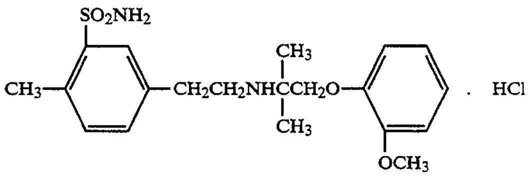

5-{2-[2-(2-Methoxyphenoxy)-1,1-dimethylethylamino]ethyl}-2-methylbenzenesulfonamide hydrochloride Physicochemical properties:

Melting point: 191°-193° C.

| Elemental analysis for $C_{20}H_{28}N_2O_4S.HCl$: | C (%) | H (%) | N (%) |
|---|---|---|---|
| Calculated: | 56.00 | 6.81 | 6.53 |
| Found: | 55.83 | 6.86 | 6.32 |

Nuclear magnetic resonance spectra ($d_6$-DMSO): δ: 1.44 (6H, s, N—C($C\underline{H}_3)_2$—C), 2.56 (3H, s,

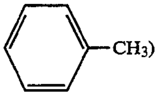

3.66 (3H, s,

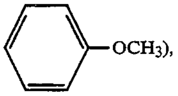

4.08 (2H, s, —$CH_2$—O)

EXAMPLE 24

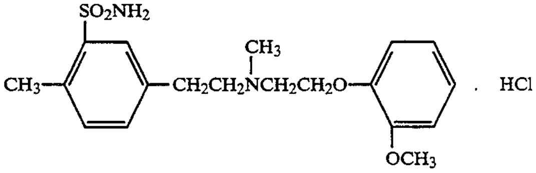

5-{2-[N-[2-(2-Methoxyphenoxy)ethyl]-N-methylamino]ethyl}-2-methylbenzenesulfonamide hydrochloride Physicochemical properties:

Melting point: 169°-171° C.

| Elemental analysis for $C_{19}H_{26}N_2O_4S.HCl$: | C (%) | H (%) | N (%) |
|---|---|---|---|
| Calculated: | 55.00 | 6.56 | 6.75 |
| Found: | 54.88 | 6.51 | 6.64 |

Nuclear magnetic resonance spectra ($d_6$-DMSO): δ: 2.56 (3H, s,

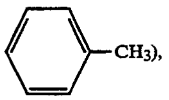

3.68 (3H, s,

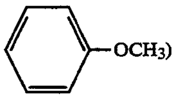

4.39 (2H, t, —$CH_2$—O)

EXAMPLE 25

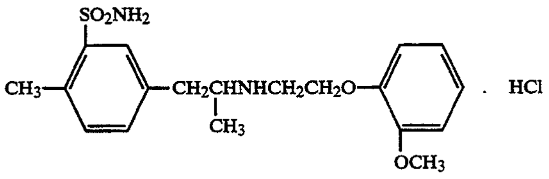

5-{2-[2-(2-Methoxyphenoxy)ethylamino]-2-methylethyl}-2-methylbenzenesulfonamide hydrochloride Physicochemical properties:

Melting point: 250°-252° C.

| Elemental analysis for $C_{19}H_{26}N_2O_4S.HCl$: | C (%) | H (%) | N (%) |
|---|---|---|---|
| Calculated: | 55.00 | 6.56 | 6.75 |
| Found: | 54.68 | 6.49 | 6.58 |

Nuclear magnetic resonance spectra ($CDCl_3$+$d_6$-DMSO+$D_2O$+$Na_2CO_3$): δ: 1.06 (3H, d,

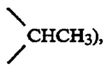
2.61 (3H, s,
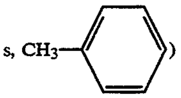

3.76 (3H, s,

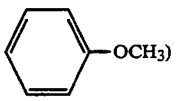

EXAMPLE 26

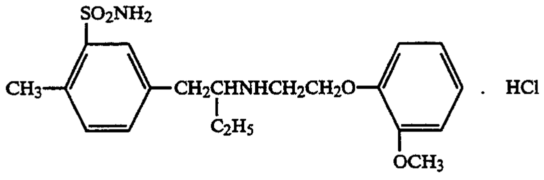

5-{2-[2-(2-Methoxyphenoxy)ethylamino]-2-ethylethyl}-2-methylbenzenesulfonamide hydrochloride Physicochemical properties:

Melting point: 198°-200° C.

| Elemental analysis for $C_{20}H_{28}N_2O_4S.HCl$: | C (%) | H (%) | N (%) |
|---|---|---|---|
| Calculated: | 56.00 | 6.81 | 6.53 |
| Found: | 55.76 | 6.88 | 6.51 |

Nuclear magnetic resonance spectra ($CDCl_3$+$d_6$-DMSO+$D_2O$+$Na_2CO_3$): δ: 0.94 (3H, t,

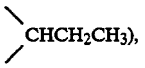
1.22 (2H, m,
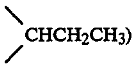

2.56 (3H, s,

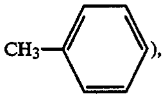

3.76 (3H, s,

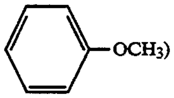

EXAMPLE 27

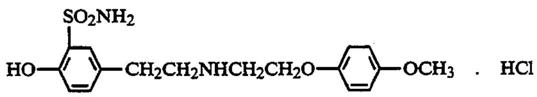

2-Hydroxy-5-{2-[2-(4-methoxyphenoxy)ethylamino]ethyl}benzenesulfonamide hydrochloride Physicochemical properties:

Melting point: 237°-241° C. (decomposed)

| Elemental analysis for $C_{17}H_{22}N_2O_5S.HCl$: | C (%) | H (%) | N (%) |
|---|---|---|---|
| Calculated: | 50.68 | 5.75 | 6.95 |
| Found: | 50.45 | 5.64 | 6.99 |

Nuclear magnetic resonance spectra ($CD_3OD$): δ: 3.74 (3H, s, O—$CH_3$), 4.22 (2H, t, —$CH_2$—O)

EXAMPLE 28

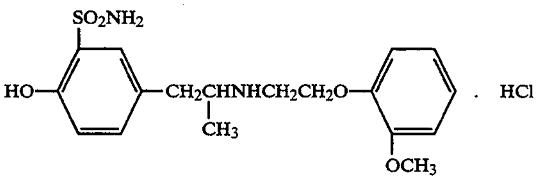

2-Hydroxy-5-{2-[2-(2-methoxyphenoxy)ethylamino]-2-methylethyl}benzenesulfonamide hydrochloride Physicochemical properties:

Melting point: 211°-214° C.

| Elemental analysis for $C_{18}H_{24}N_2O_5S.HCl$: | C (%) | H (%) | N (%) |
|---|---|---|---|
| Calculated: | 51.86 | 6.04 | 6.72 |
| Found: | 51.72 | 6.00 | 6.59 |

Nuclear magnetic resonance spectra ($CD_3OD$): δ: 1.28 (3H, d,

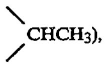

3.86 (3H, s, —$OCH_3$) 4.30 (2H, t, —$CH_2$—O),

EXAMPLE 29

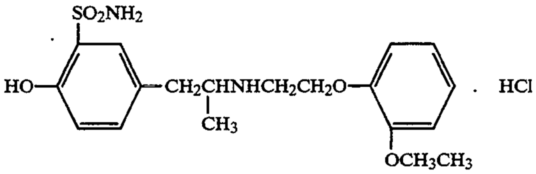

5-{2-[2-(2-Ethoxyphenoxy)ethylamino]-2-methylethyl}-2-hydroxybenzenesulfonamide hydrochloride Physicochemical properties:

Melting point: 172°-173° C.

| Elemental analysis for $C_{19}H_{26}N_2O_5S.HCl$: | C (%) | H (%) | N (%) |
|---|---|---|---|
| Calculated: | 52.96 | 6.31 | 6.50 |
| Found: | 52.83 | 6.65 | 6.12 |

Nuclear magnetic resonance spectra ($CD_3OD$): 1.26 (3H, d,

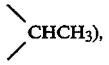

1.36 (3H, t, —$CH_2CH_3$) 4.10 (2H, q, —$CH_2CH_3$), 4.26 (2H, t, —$CH_2CH_2$—O)

EXAMPLE 30 (a)

In 6 ml of pyridine was dissolved 1.5 g of (−)-2-(p-methoxyphenyl)-1-methylethylamine ($[\alpha]_D^{23}$: −30.1° (c=1.2, methanol)), and after adding thereto 3 ml of acetic anhydride, the mixture was allowed to stand at room temperature for 1 hour. After distilling off the solvent, the residue was extracted with ethyl acetate. The ethyl acetate extract was washed with water, and dried over anhydrous sodium sulfate, and the solvent was distilled off and the crude crystals formed were recrystallized from a mixture of n-hexane and benzene to provide 1.8 g of (R)(+)-N-acetyl-2-(p-methoxyphenyl)-1-methylethylamine.

Melting point: 92°-93° C.

| Elemental analysis for $C_{12}H_{17}NO_2$: | C (%) | H (%) | N (%) |
|---|---|---|---|
| Calcd.: | 69.54 | 8.27 | 6.76 |
| Found: | 69.41 | 8.19 | 6.66 |

$[\alpha]_D^{24}$: 14.8° (c=1.09, methanol)

EXAMPLE 30 (b)

By following the same procedure as in Example 30 (a), (S)(−)-N-acetyl-2-(p-methoxyphenyl)-1-methylethylamine was obtained by using (+)-2-(p-methoxyphenyl)-1-methylethylamine ($[\alpha]_D^{24}$: 29.9° (c=1, methanol)) as the starting material.

Melting point: 94°-96° C. (n-hexane-benzene)

| Elemental analysis for $C_{12}H_{17}NO_2$: | C (%) | H (%) | N (%) |
|---|---|---|---|
| Calcd.: | 69.54 | 8.27 | 6.76 |
| Found: | 69.41 | 8.19 | 6.66 |

$[\alpha]_D^{24}$: −15.3 (c=1.25, methanol)

EXAMPLE 31 (a)

In 60 g of chlorosulfonic acid was added 6 g of (R)(+)-N-acetyl-2-(p-methoxyphenyl)-1-methylethylamine, under cooling at 0° to −10° C. The mixture was stirred for 1 hour at 0° to 5° C., and the reaction solution was poured into 600 g of ice-water. The oily material precipitated was extracted with ethyl acetate, and the ethyl acetate extract was washed with a saturated aqueous sodium hydrogen carbonate solution and dried over anhydrous sodium sulfate. After distilling off the solvent, the formed residue (without purification) was dissolved in 120 ml of tetrahydrofuran. After adding dropwise thereto 180 ml of a concentrated aqueous ammonia solution, the mixture was stirred for 1 hour at room temperature. The crystals precipitated were collected by filtration, washed with water, and recrystallized from methanol to provide 6 g of (R)(+)-N-acetyl-5-[(2-amino-2-methyl)ethyl]-2-methoxybenzenesulfonamide.

Melting point: 197°-198° C.

| Elemental analysis for $C_{12}H_{18}N_2O_4S$: | C (%) | H (%) | N (%) |
|---|---|---|---|
| Calcd.: | 50.34 | 6.34 | 9.78 |
| Found: | 50.28 | 6.41 | 9.69 |

$[\alpha]_D^{24}$: 14.7° (c=1.0, methanol)

EXAMPLE 31 (b)

By following the same procedure as in Example 31 (a), (S)(−)-N-acetyl-5-[(2-amino-2-methyl)ethyl]-2-methoxybenzenesulfonamide by using (S)(−)-N-acetyl- 2-(p-methoxyphenyl)-1-methylethylamine as the starting material.

Melting point: 196°-198° C. (methanol)

| Elemental analysis for $C_{12}H_{18}N_2O_4S$: | C (%) | H (%) | N (%) |
|---|---|---|---|
| Calcd.: | 50.34 | 6.34 | 9.78 |
| Found: | 50.31 | 6.24 | 9.73 |

$[\alpha]_D{}^{-24}$: −14.2° (c=1.01, methanol)

EXAMPLE 32 (a)

5 g of (R)(+)-N-acetyl-5-[(2-amino-2-methyl)ethyl]-2-methoxybenzenesulfonamide was dissolved in 125 ml of 5% hydrochloric acid, and the solution was refluxed under heating for 16 hours. After distilling off the solvent, the crude crystals formed were recrystallized from isopropanol to provide 4.5 g of (R)(−)-5-[(2-amino-2-methyl)ethyl]-2-methoxybenzenesulfonamide.

Melting point: 273°-277° C. (decomposition)

| Elemental analysis for $C_{10}H_{17}ClN_2O_3S$: | C (%) | H (%) | N (%) |
|---|---|---|---|
| Cacld.: | 42.78 | 6.10 | 9.98 |
| Found: | 42.68 | 6.00 | 9.93 |

$[\alpha]_D{}^{24}$: −6.3° (c=1.03, methanol)

EXAMPLE 32 (b)

By following the same procedure as in Example 32 (a), (S)(+)-5-[(2-amino-2-methyl)ethyl]-2-methoxybenzenesulfonamide was obtained by using (S)(−)-N-acetyl-5-[(2-amino-2-methyl)ethyl]-2-methoxybenzenesulfonamide as the starting material.

Melting point: 273°-276° C. (decomposition)

| Elemental analysis for $C_{10}H_{17}ClN_2O_3S$: | C (%) | H (%) | N (%) |
|---|---|---|---|
| Cacld.: | 42.78 | 6.10 | 9.98 |
| Found: | 42.65 | 6.03 | 9.89 |

$[\alpha]_D{}^{24}$: 6.0 (c=1.01, methanol)

EXAMPLE 33 (a)

In 120 ml of ethanol were dissolved 2.4 g of (R)(−)-5-[(2-amino-2-methyl)ethyl]-2-methoxybenzenesulfonamide and 1.2 g of 2-(o-ethoxyphenoxy)ethyl bromide, and the mixture was refluxed for 16 hours under heating. The solvent was distilled away, and after alkalifing the residue by the addition of 10% sodium hydroxide, and the oily material precipitated was extracted with ethyl acetate. The extract solution was washed with a saturated aqueous sodium chloride, and dried over anhydrous magnesium sulfate. The solvent was distilled away, and the residue was subjected to silica-gel column chromatography. The product was eluted with $CHCl_3$-methanol (9:5) to provide 1.5 g of the crude crystals of (R)(−)-5-[2-[[2-(o-ethoxyphenoxy)ethyl]amino]-2-methylethyl]-2-methoxybenzenesulfonamide, which was treated with HCl-ethanol to give a hydrochloric acid salt of (R)(−)-5-[2-[[2-(o-ethoxyphenoxy)ethyl]amino]-2-methylethyl]-2-methoxybenzenesulfonamide.

Melting point: 228°-230° C.

| Elemental analysis for $C_{20}H_{29}ClN_2O_5S$: | C (%) | H (%) | N (%) |
|---|---|---|---|
| Cacld.: | 53.99 | 6.57 | 6.30 |
| Found: | 53.90 | 6.64 | 6.27 |

$[\alpha]_D{}^{-24}$: −4.0° (c=0.35, methanol)

EXAMPLE 33 (b)

By following the same procedure as in Example 33 (a), (S)(+)-5-[2-[[2-(o-ethoxyphenoxy)ethyl]amino]-2-methylethyl]-2-methoxybenzenesulfonamide was obtained by using (S)(+)-5-[(2-amino-2-methyl)ethyl]-2-methoxybenzenesulfonamide as the starting material.

Melting point: 228°-230° C. (methanol)

| Elemental analysis for $C_{20}H_{29}ClN_2O_5S$: | C (%) | H (%) | N (%) |
|---|---|---|---|
| Cacld.: | 53.99 | 6.57 | 6.30 |
| Found: | 53.92 | 6.57 | 6.45 |

$[\alpha]_D{}^{24}$: 4.2° (c=0.36, methanol)

What is claimed is:

1. The R(−)-isomer of the following compound:

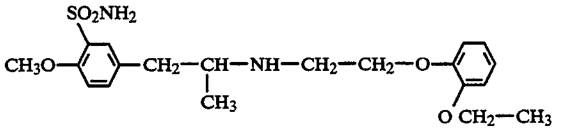

2. A pharmaceutical composition containing the compound of claim 1 as an active component and a pharmaceutically acceptable carrier.

* * * * *

Disclaimer 5,447,958—Kunihiro Niigata; Takashi Fujikura, both of Saitama, Japan. SULFAMOYL-SUBSTITUTED PHENETHYLAMINE DERIVATIVES, THEIR PREPARATION, AND PHARMACEUTICAL COMPOSITIONS, CONTAINING THEM. Patent dated September 5, 1995. Disclaimer filed Jun. 25, 2004, by the assignee, Yamanouchi Pharmaceutical Co., Ltd.

Hereby enters this disclaimer to all claims of said patent.

*(Official Gazette, August 17, 2004)*